US011147505B1

(12) United States Patent
Shoeb et al.

(10) Patent No.: US 11,147,505 B1
(45) Date of Patent: Oct. 19, 2021

(54) METHODS, SYSTEMS AND DEVICES FOR IDENTIFYING AN ABNORMAL SLEEP CONDITION

(71) Applicant: Verily Life Sciences LLC, Mountain View, CA (US)

(72) Inventors: Ali Shoeb, Mill Valley, CA (US); Russell Norman Mirov, Los Altos, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 360 days.

(21) Appl. No.: 14/727,808

(22) Filed: Jun. 1, 2015

(51) Int. Cl.
*A61B 5/00* (2006.01)
*A61B 5/0205* (2006.01)
(Continued)

(52) U.S. Cl.
CPC .......... *A61B 5/4809* (2013.01); *A61B 5/0205* (2013.01); *A61B 5/4812* (2013.01); *A61B 5/4815* (2013.01); *A61B 5/6801* (2013.01); *A61B 5/7282* (2013.01); *A61B 5/7455* (2013.01); *A61M 16/0003* (2014.02); (Continued)

(58) Field of Classification Search
CPC ... A61B 5/4809; A61B 5/0205; A61B 5/4812; A61B 5/6801; A61B 5/7282; A61B 5/7455; A61B 5/02416; A61B 5/0816; A61B 5/1116; A61B 7/003; A61B 5/4815; A61M 16/0003; A61M 2205/3331
See application file for complete search history.

(56) References Cited

U.S. PATENT DOCUMENTS 5,199,424 A * 4/1993 Sullivan ................. A61B 5/097
128/204.18
7,656,287 B2 2/2010 Albert et al.
(Continued)

FOREIGN PATENT DOCUMENTS

WO 2014/210588 12/2014

OTHER PUBLICATIONS http://www.itamar-medical.com/images/WatchPAT%208pagesBro%20Low.pdf.
(Continued)

*Primary Examiner* — Gary Jackson
*Assistant Examiner* — Jessandra F Hough
(74) *Attorney, Agent, or Firm* — McDonnell Boehnen Hulbert & Berghoff LLP

(57) ABSTRACT

Methods, systems, and devices for identifying abnormal sleep conditions are disclosed. During each of a plurality of non-zero time periods, a wearable device configured to be worn on a body of a user may capture (i) a physiological parameter measurement and (ii) a non-physiological parameter measurement, thereby providing a plurality of physiological parameter measurements and a plurality of non-physiological parameter measurements, respectively. Based at least in part on the plurality of physiological parameter measurements and the plurality of non-physiological parameter measurements, the wearable device may identify an abnormal sleep condition. Responsive to identifying the abnormal sleep condition, the wearable device may cause an output device to provide a notification, with the output device being a part of or connected to the wearable device.

20 Claims, 6 Drawing Sheets

(51) Int. Cl.
*A61M 16/00* (2006.01)
*A61B 5/024* (2006.01)
*A61B 5/08* (2006.01)
*A61B 7/00* (2006.01)
*A61B 5/11* (2006.01)

(52) U.S. Cl.
CPC ......... *A61B 5/02416* (2013.01); *A61B 5/0816* (2013.01); *A61B 5/1116* (2013.01); *A61B 7/003* (2013.01); *A61M 2205/3331* (2013.01)

(56) References Cited

U.S. PATENT DOCUMENTS

| | | | |
|---|---|---|---|
| 9,005,129 B2 | 4/2015 | Venkatraman et al. | |
| 2008/0033304 A1* | 2/2008 | Dalal | A61B 5/0205 600/484 |
| 2009/0121826 A1* | 5/2009 | Song | A61B 5/6887 340/3.1 |
| 2011/0034811 A1* | 2/2011 | Naujokat | A61B 5/4809 600/484 |
| 2012/0116187 A1* | 5/2012 | Hayes | A61B 5/11 600/301 |
| 2013/0079606 A1 | 3/2013 | McGonigle et al. | |
| 2013/0079647 A1 | 3/2013 | McGonigle et al. | |
| 2013/0079656 A1 | 3/2013 | Dripps et al. | |
| 2013/0079657 A1 | 3/2013 | Ochs et al. | |
| 2014/0073976 A1* | 3/2014 | Fonte | A61B 6/504 600/504 |
| 2014/0194793 A1 | 7/2014 | Nakata et al. | |
| 2014/0275852 A1* | 9/2014 | Hong | A61B 5/02427 600/301 |
| 2014/0275889 A1 | 9/2014 | Addison et al. | |
| 2014/0276175 A1* | 9/2014 | Banet | A61B 5/0402 600/536 |
| 2014/0316230 A1* | 10/2014 | Denison | A61B 5/04012 600/383 |
| 2015/0112452 A1 | 4/2015 | He et al. | |
| 2015/0208964 A1 | 7/2015 | Addison et al. | |

OTHER PUBLICATIONS http://www.itamar-medical.com/images/TrueSleepTime%20-%20one%20page%20-%20LOW.pdf.
http://www.itamar-medical.com/images/TotalSleepSolution-10.2015.pdf.
Li et al., "Comparison of respiratory-induced variations in photoplethysmographic signals", Physiol. Meas. 31 (2010), pp. 415-425.
Scholkmann et al., "An Efficient Algorithm for Automatic Peak Detection in Noisy Periodic and Quasi-Periodic Signals", Algorithms 2012, 5, pp. 588-603.
Karlen et al., "Multiparameter Respiratory Rate Estimation From the Photoplethysmogram", IEEE Transactions on Biomedical Engineering, vol. 60, No. 7, Jul. 2013.

* cited by examiner

METHODS, SYSTEMS AND DEVICES FOR IDENTIFYING AN ABNORMAL SLEEP CONDITION

BACKGROUND

Unless otherwise indicated herein, the materials described in this section are not prior art to the claims in this application and are not admitted to be prior art by inclusion in this section.

Restful sleep provides a number of important benefits to people, such as improved alertness, memory, reflexes, and focus, as well as time for the body to heal. A number of abnormal sleep conditions may prevent individuals from getting restful sleep. Failure to achieve restful sleep, especially over a period of time, may deprive a person of the benefits of restful sleep. Moreover, a prolonged absence of restful sleep may increase the risk of obesity, heart disease, and infection, among other ailments. One such abnormal sleep condition is sleep apnea, which generally refers to a condition in which an individual momentarily stops breathing while asleep. A person suffering from sleep apnea might experience dozens of episodes of sleep apnea in a given night, each of which may disrupt the person's normal sleep cycle. Another abnormal sleep condition is somnambulism, more commonly referred to as sleepwalking.

SUMMARY

In one aspect, a method is disclosed. During each of a plurality of non-zero time periods, the method includes a wearable device configured to be worn on a body of a user capturing (i) a physiological parameter measurement and (ii) a non-physiological parameter measurement, thereby providing a plurality of physiological parameter measurements and a plurality of non-physiological parameter measurements, respectively. For each non-zero time period, the method includes determining from the plurality of physiological parameter measurements a mean of a physiological parameter and a variance of the physiological parameter, thereby providing a plurality of physiological parameter means and a plurality of physiological parameter variances. Based at least in part on the plurality of physiological parameter means, the plurality of physiological parameter variances, and the plurality of non-physiological parameter measurements, the method includes the wearable device identifying an abnormal sleep condition. Responsive to identifying the abnormal sleep condition, the method includes the wearable device causing an output device to provide a notification, with the output device being a part of or connected to the wearable device.

In another aspect, a wearable device is disclosed. The wearable device includes a first sensor configured to measure a physiological parameter, a second sensor configured to measure a non-physiological parameter, an output device, and a processor. The processor is configured to, during each of plurality of non-zero time periods, (a) receive from the first sensor a measurement of the physiological parameter, thereby providing a plurality of physiological parameter measurements, and (b) receive from the second sensor a measurement of the non-physiological parameter, thereby providing a plurality of non-physiological parameter measurements. For each non-zero time period, the processor is configured to determine from the plurality of physiological parameter measurements a mean of a physiological parameter and a variance of the physiological parameter, thereby providing a plurality of physiological parameter means and a plurality of physiological parameter variances. The processor is further configured to identify, based at least in part on the plurality of physiological parameter means, the plurality of physiological parameter variances, and the plurality of non-physiological parameter measurements, an abnormal sleep condition.

In still another aspect, a system is disclosed. The system comprises means included in a wearable device for capturing, during each of a plurality of non-zero time periods, a physiological parameter measurement and a non-physiological parameter measurement, thereby providing a plurality of physiological parameter measurements and a plurality of non-physiological parameter measurements, respectively. The system also comprises means included in the wearable device for determining, for each non-zero time period and from the plurality of physiological parameter measurements, a mean of a physiological parameter and a variance of the physiological parameter, thereby providing a plurality of physiological parameter means and a plurality of physiological parameter variances., a. The system may additionally include means for identifying, based at least in part on the plurality of physiological parameter means, the plurality of physiological parameter variances, and the plurality of non-physiological parameter measurements, an abnormal sleep condition. The system may further include means for causing, in response to identifying the abnormal sleep condition, an output device connected to the wearable device to provide a notification.

These as well as other aspects, advantages, and alternatives, will become apparent to those of ordinary skill in the art by reading the following detailed description, with reference where appropriate to the accompanying drawings.

DETAILED DESCRIPTION

Figure 1:
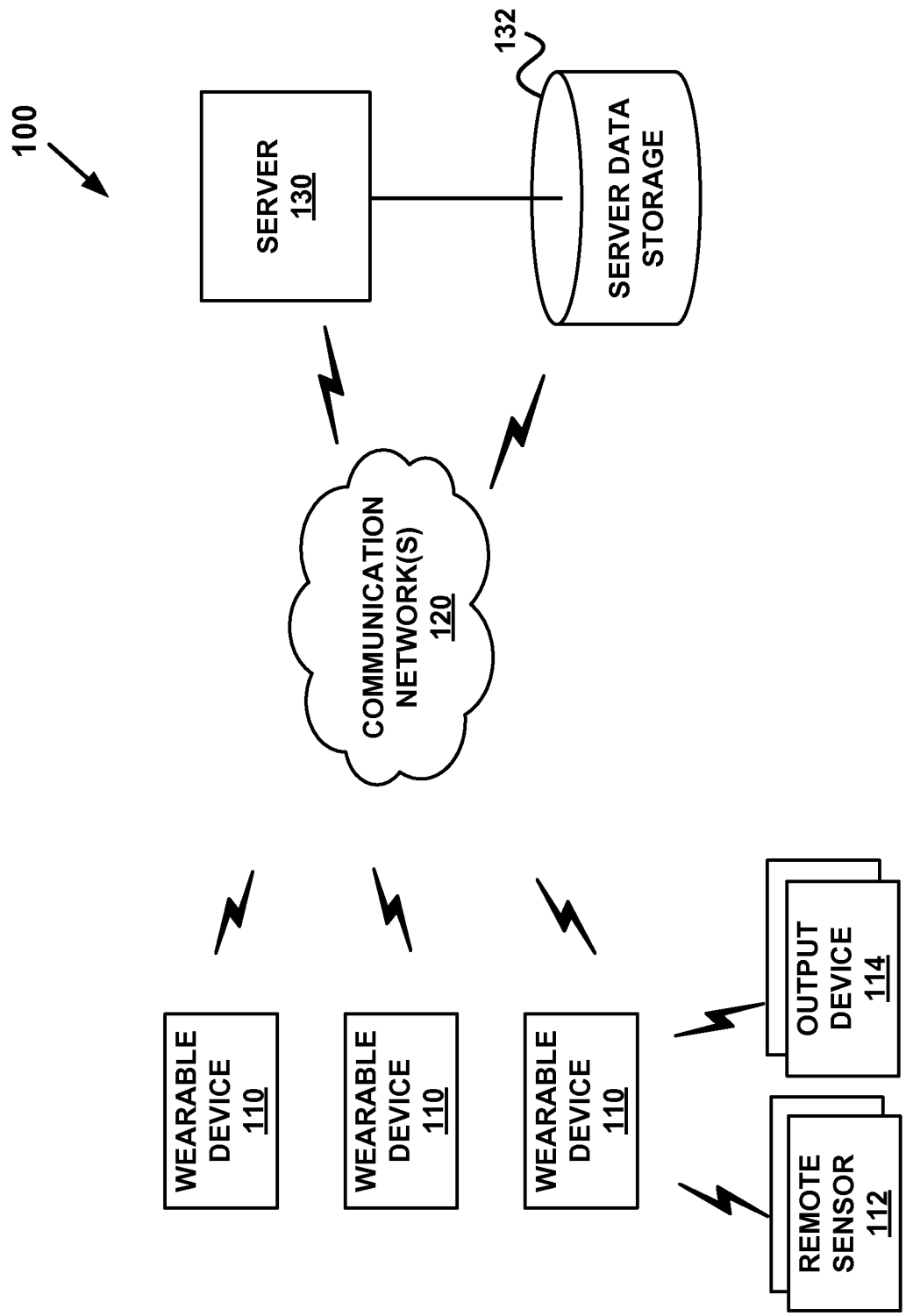
FIG. 1 is a block diagram of an example health monitoring system that includes a plurality of electronic devices in communication with a server.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

A normal night of restful sleep refers to seven to ten hours of continuous, uninterrupted sleep that follows a standard sleep cycle transition from non-rapid eye movement (NREM) sleep to rapid-eye movement (REM) sleep: stage 1 NREM sleep, stage 2 NREM sleep, stage 3 NREM sleep, rapid-eye movement (REM) sleep, stage 1 NREM sleep, etc. A number of abnormal sleep conditions may prevent a person from achieving restful sleep. Typically, diagnosis of an abnormal sleep condition involves a sleep study in which a physician and/or other medical professional(s) monitor a person's sleep throughout a night. Such sleep studies can be costly and are often inconvenient. Further, some people may not achieve restful sleep on account of being monitored and/or due to sleeping in an unfamiliar environment. Thus, some people may benefit from a more convenient, less intrusive means for identifying an abnormal sleep condition. Moreover, the availability of a personal sleep monitoring device may be desirable, as such a device would allow for more frequent (if not continuous) sleep monitoring thereby minimizing the need for multiple sleep studies and identification of trends or conditions that might not be detected during a sleep study.

Embodiments described herein are directed to aspects of a wearable device configured to detect indications of an abnormal sleep condition, such as sleep apnea and/or sleepwalking, for instance. In response to detecting the abnormal sleep condition, the wearable device may cause an output device to provide a notification, with the output device being either a part of or connected to the wearable device. As used herein, a notification refers to a tactile output, an audible output, a visual output, or another type of perceptible output that a user of the wearable device, and possibly another person or animal (e.g., a service animal) in the vicinity of the user, can perceive. By providing the notification, the wearable device may remedy the abnormal sleep condition, thereby allowing the user to achieve more restful sleep in many situations.

In an example method, a wearable device (e.g., an electronic device configured to be worn on a body of a user) may capture, during each of a plurality of non-zero time periods, a physiological parameter measurement, thereby providing a plurality of physiological parameter measurements. By way of example, the plurality of physiological parameter measurements may include a plurality of photoplethysmographic (PPG) signals. Here, the wearable device may include one or more sensors configured to illuminate a portion of the user's skin and detect reflected light. From the reflected light received over a non-zero time period (e.g., about thirty seconds), the wearable device may generate a PPG signal that includes data indicative of an intensity, wavelength, and/or other parameter of detected light. The wearable device may extract from each PPG signal one or more physiological parameters, thereby providing a plurality physiological parameters from which the wearable device may determine one or more statistics. For instance, the wearable device may determine a mean and a variance of a physiological parameter (e.g., a heart rate or a respiration rate) over a period of time, thereby providing a plurality of physiological parameter means and a plurality of physiological parameter variances.

The example method also includes, for each of the plurality of non-zero time periods, capturing by the wearable device a non-physiological parameter measurement, thereby providing a plurality of non-physiological parameter measurements. As one example, the wearable device may include an inertial measurement unit (IMU), and the non-physiological parameter may be a movement of the user. As another example, the wearable device may include a microphone, and the non-physiological parameter may be indicative of an amplitude and frequency of sounds received at the microphone, and possibly recorded, during the non-zero time period.

The example method further includes identifying an abnormal sleep condition based at least in part on the plurality of physiological parameter measurements and the plurality of non-physiological parameter measurements. By way of example, the wearable device may receive from a server (or another computing device) data for determining a sleep stage from the plurality of physiological measurements. For instance, the wearable device may receive from a server data indicative of values for physiological parameters and non-physiological parameters, perhaps in the form of one or more vectors, that are indicative of different abnormal sleep conditions. Such data may be generated by a server-implemented machine-learning algorithm that receives a plurality of physiological parameter measurements from each of a plurality of wearable devices. Using the received data, the wearable device may determine from the plurality of physiological parameter measurements a sleep stage cycle. If the current sleep stage is not consistent with the normal progression of sleeps stages—stage 1 sleep, stage 2 sleep, stage 3 sleep, rapid eye movement (REM) sleep—then the wearable device may identify an abnormal sleep condition. Moreover, the wearable device may identify the abnormal sleep condition by determining that the determined sleep stage cycle correlates to a particular abnormal sleep condition or set of abnormal sleep conditions.

To further identify the abnormal sleep condition, the wearable device may determine whether one or more non-physiological parameter measurements are indicative of an abnormal sleep condition. For instance, if the wearable device includes an IMU, then the wearable device may determine from the plurality of non-physiological measurements whether the user is supine (i.e., lying on the user's back). Additionally or alternatively, if the wearable device includes a microphone, the wearable device may determine whether sounds received by the microphone are consistent with the user snoring. When coupled with the determined sleep stage cycle, the wearable device may identify sleep apnea as the abnormal sleep condition.

As another example, consider a situation in which the wearable device determines that the user is asleep. The wearable may also receive from the IMU signals that include detected movements of the wearable device, which the wearable device may determine are indicative of the user walking. In this event, the wearable device may identify sleepwalking as the abnormal sleep condition.

In response to identifying the abnormal sleep condition, the example method includes the wearable device causing an output device to provide a notification, with the output device being either a part of or connected to the wearable device. Whether the notification wakes the user may depend on the identified abnormal sleep condition. In most situations, the notification may be subconsciously perceived by the recipient, thereby reducing the temporal length of the abnormal sleep condition and allowing the user to return to a standard sleep cycle. For example, consider a situation in which the wearable device includes an electro-mechanical transducer. If the wearable device identifies sleep apnea as the abnormal sleep condition, the wearable device may cause the electro-mechanical transducer to provide a low-intensity vibration to the user's body. Such a perceptible output against the user's body could cause the user to roll onto the user's side, thereby positioning the user so as to minimize the time the user is supine. In another example, the wearable device may be connected to a continuous positive airway pressure (CPAP) device, which provides a positive pressure to the user's airway so as to minimize or prevent sleep apnea. In response to identifying sleep apnea as the abnormal sleep condition, the wearable device may send a signal to a control unit of the CPAP device, and the signal may cause the control unit to increase the pressure applied to the user's airway. The increased pressure may allow the user to breath normally, thereby reducing the likelihood that a sleep apnea event disturbs the user's sleep.

In the two preceding examples, the notification may not wake the user, thereby facilitating the user staying in a normal sleep cycle. But waking the user may be desirable in some examples. One such example may be when the wearable device determines that the user is sleepwalking. Since the user may sustain an injury while sleepwalking, the notification can be of sufficient intensity to wake the user. If the wearable device includes an electro-mechanical transducer, then the wearable device may cause the electro-mechanical transducer to vibrate at an intensity that is likely to wake the user. Additionally or alternatively, the wearable device may be connected to a speaker or similar audio output component, in which case the wearable device may cause the speaker to provide the notification as an audible alarm at a volume (i.e., loudness) that is likely to wake the user. Moreover, the wearable device could be connected to a remote device that has a speaker, such as a smartphone, alarm clock, etc., and the wearable device could send a signal to the remote device that causes the remote device to output the alarm. Advantageously, the alarm may wake up the user and/or another person in the vicinity of the user, thereby minimizing the risk of the user sustaining an injury while sleepwalking.

II. EXAMPLE SYSTEMS AND SYSTEM COMPONENTS

Turning now to the figures, FIG. 1 is a simplified schematic of a health monitoring system 100 that includes wearable devices 110. A user may wear one of the wearable device 110 and possibly one or more remote sensors 112 that communicate with the user's wearable device 110. Each wearable device 110 may capture and/or receive from the sensor(s) 112 a plurality of physiological parameter measurements and a plurality of non-physiological para parameter measurements. The user's wearable device 110 may also communicate with one or more output devices 114, which may provide a notification. By way of example, the notification may be an audible, tactile, or visual, and the one or more output devices 114 may include smartphones, alarm clocks, tablet computers, or another electronic device capable of providing one or more notifications.

The wearable devices 110 may also communicate with a server 130 via a communication network 120, perhaps by a wireline connection and/or a wireless connection. The communication network 120 may include one or more of a plain old telephone service (POTS) network, a cellular network, a fiber-optic network, or a data network. The server 130 may communicate with the wearable devices 110 according to one or more network protocols and/or application-level protocols to facilitate the use of network-based or cloud-based computing on client devices. The server 130 may include integrated data storage (e.g., memory, disk drives, etc.) and may also be able to access a separate server data storage 132. Communication between the server 130 and the server data storage 132 may be direct (e.g., via a wireline or via a local wireless communication link) and/or via the communication network 120. The server data storage 132 may store application data that is used to facilitate the operations of applications performed by the wearable devices 110 and/or the server 130.

Additionally or alternatively, the server 130 and the server data storage 132 may store applications and application data at one or more places accessible via communication network 120. These places may be data centers containing numerous servers and storage devices. The exact physical location, connectivity, and configuration of the server 130 and the server data storage 132 may be unknown and/or unimportant to client devices (e.g., the wearable devices 110). Accordingly, the server 130 and the server data storage device 132 may be referred to as "cloud-based" devices that are housed at various remote locations. One possible advantage of such "cloud-based" computing is to offload processing and data storage from client devices, thereby simplifying the design and requirements of these client devices.

In some embodiments, the server 130 and the server data storage 132 may be a single computing system residing in a single data center. In other embodiments, the server 130 and the server data storage 132 may include multiple computing systems in a data center, or even multiple computing systems in multiple data centers, where the data centers are located in diverse geographic locations. For example, FIG. 1 depicts each of the server 130 and the server data storage device 132 as potentially residing in different physical locations.

In addition to receiving communications from the wearable devices 110, such as data indicative of physiological and non-physiological parameter measurements, the server 130 may also be configured to gather and/or receive, from either each wearable device 110 or some other source(s) (not shown), information regarding a user's overall medical history, environmental factors and geographical data. For example, the server 130 and/or the server data storage 132 may include a user account for every user that contains the user's medical history.

Moreover, in some examples, the server 130 may be configured to regularly receive other information, such as viral illness or food poisoning outbreak data from the Centers for Disease Control (CDC) and weather, pollution and allergen data from the National Weather Service. Further, the server 130 may be configured to receive data regarding a user's health state from a hospital or physician. Such information may be used in a machine-learning algorithm implemented by the server 130, which may identify vectors of physiological and/or non-physiological parameters corresponding to abnormal sleep conditions.

Additionally, the server 130 may be configured to gather and/or receive the date, time of day and geographical location of each wearable device 110 during each measurement period. In measuring physiological parameters of the user (e.g., extracted PPG waveforms), such information may be used to detect and monitor spatial and temporal spreading of diseases, which may affect a given users' ability to achieve restful sleep. As such, the wearable devices 110 may be configured to determine and/or provide an indication of its own location. For example, an electronic device may include a GPS system so that it can include GPS location information (e.g., GPS coordinates) in a communication to the server. As another example, a wearable device may use a technique that involves triangulation (e.g., between base stations in a cellular or Bluetooth® network) to determine its location. Other location-determination techniques are also possible.

Further, some embodiments of the system may include privacy controls which may be automatically implemented or controlled by the user of each wearable device 110. For example, where a user's collected data are uploaded to a cloud computing network for analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, the user of each wearable devices 110 may be provided with an opportunity to control whether or how the wearable device 110 collect information about the user (e.g., information about a user's medical history, social actions or activities, profession, a user's preferences, or a user's current location), or to control how such information may be used. Thus, the user may have control over how information is collected about him or her and used by a clinician or physician or other user of the data. For example, a user may elect that data, such as health state and physiological parameters, collected from his or her device may only be used for generating an individual baseline and recommendations in response to collection and comparison of his or her own data and may not be used in generating a population baseline or for use in population correlation studies.

Although only three wearable devices 110, one server 130, and one server data storage 132 are shown in FIG. 1, remote health monitoring system 100 may include any number of each of these components. For instance, the health monitoring system 100 may include thousands of electronic devices, thousands of servers, and/or thousands of server data storages. Further, while FIG. 1 depicts only one wearable device 110 as being connected to the remote sensors(s) 112 and the output device(s) 114, each wearable device 110 in the remote health monitoring system 100 may be connected to one or more sensors and/or output devices.

Figure 2:
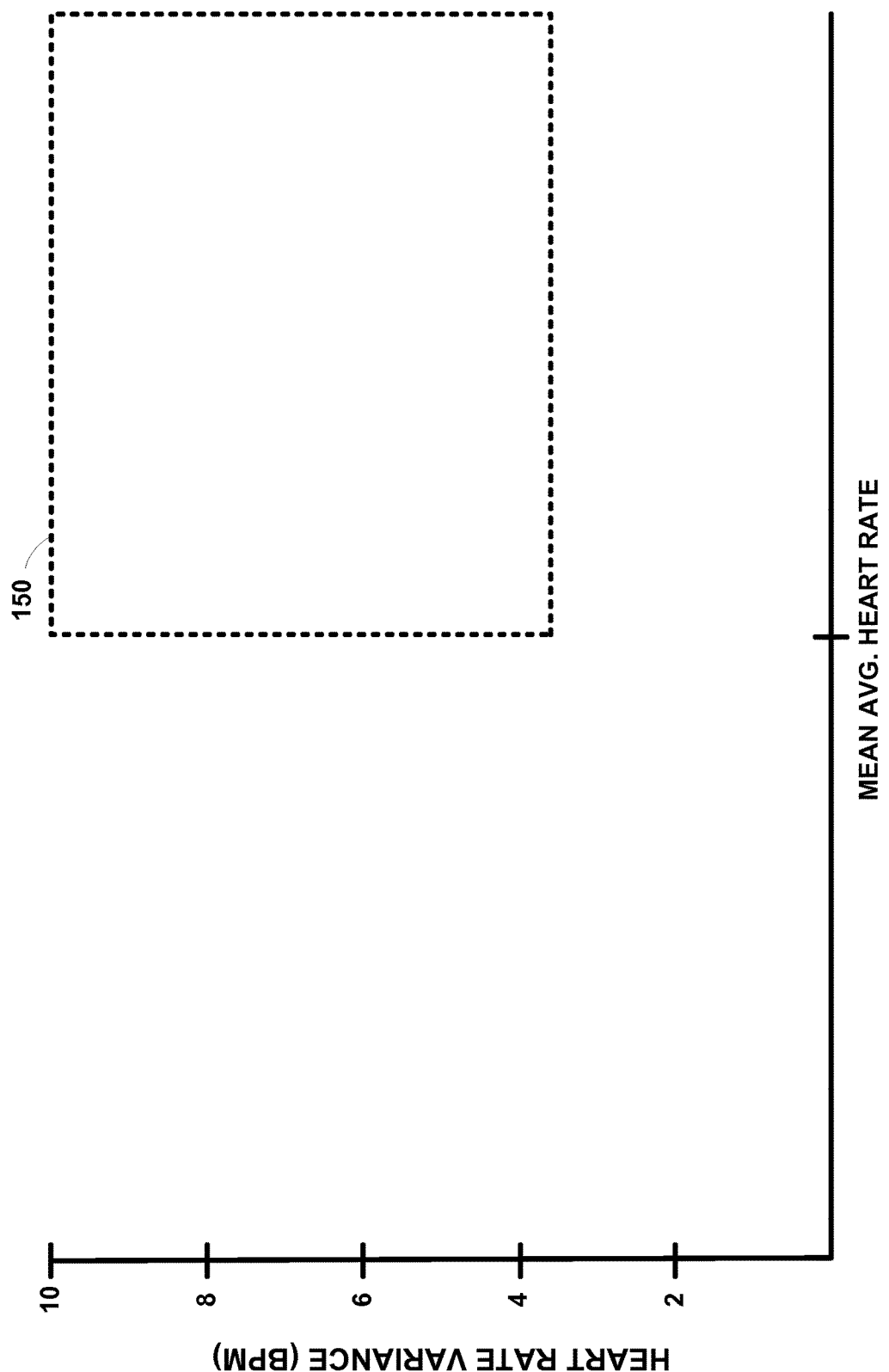
FIG. 2 is a graph of an average heart rate versus a variance in the average heart rate.

In line with the discussion above, a user may wear one the wearable devices 110 to identify an abnormal sleep condition. In an example operation, the server 130 may receive from the wearable devices 110 a plethora of physiological parameter measurements and non-physiological parameter measurements measured over a number of sleep periods. Whereas the physiological parameter measurements may include PPG signals, Galvanic skin measurements, and/or skin temperatures, the non-physiological parameter measurements may include measurements indicative of movements of the wearable device 110 and/or audio recordings. From the received plethora of physiological parameter and non-physiological parameter measurements and, the server 130 may implement a machine-learning algorithm to determine vectors of parameters that correlate to one or more abnormal sleep conditions. To this end, the physiological measurements may include a number of electroencephalograph (EEG) signals. For a given user at a given time, the server 130 may determine a sleep state from the brain activity included in one of the EEG signals, and the server 130 may thus use the machine-learning algorithm to identify vectors of parameters that correlate to various sleep stages. For instance, FIG. 2 shows a graph of average pulse rates versus pulse rate variances. In implementing the machine-learning algorithm, the server 130 may determine from the received plethora of physiological parameter measurements that pulse rate mean-pulse rate variance falling on or within an area 200 correlates to REM sleep. Note that in other examples the vector may be more than a two-dimensional vector. Moreover, the server 130 could determine user-specific sets of vectors based on physiological parameter measurements received from a single wearable device 110.

Further, the machine-learning algorithm may be trained to determine sets of vectors that correlate to each of one or more abnormal sleep conditions. Here, the vector for a given abnormal sleep condition may include ranges and/or thresholds for one or more physiological parameters and one or more non-physiological parameters. The server 130 may then send the determined sets of vectors to the wearable devices 110.

Before the user goes to sleep, the user of a wearable device 110 may interact with the wearable device to initiate a sleep-monitoring program. The wearable device 110 may then measure physiological parameters and non-physiological parameters over non-zero time periods (e.g., every thirty seconds). The wearable device 110 may then determine from the measured parameters whether the user is experiencing an abnormal sleep condition. Alternatively, if the wearable device 110 is connected to the server 130, perhaps via a wireless connection to a smartphone, a tablet computer, and/or a cellphone, the wearable device 110 may send the measured data to the server 130, and the server 130 may determine whether the user is experiencing an abnormal sleep condition.

Responsive to determining that the user is experiencing an abnormal sleep condition, the wearable device 110 may identify the abnormal sleep condition and responsively provide a notification. As one example, the wearable device 110 may determine from a plurality of PPG signals that the user is in stage 3 NREM sleep or REM sleep, and the wearable device 110 may measure one or more movements indicative of the user being supine and/or receive sounds indicative of the user snoring. From such measurements, the wearable device 110 (or alternatively the server 130) may identify sleep apnea as the abnormal sleep condition. The wearable device 110 may responsively cause a component of the wearable device 110, such as an electro-mechanical transducer, to provide a notification to the recipient, perhaps in the form of a low-intensity vibration applied to the user's wrist (or otherwise to the location at which the recipient wears the wearable device 110). The low-intensity vibration may cause the user to roll on to the user's side without waking the user, thereby alleviating the abnormal sleep condition while also allowing the user to remain asleep. This may allow the user to experience uninterrupted, more restful sleep. In another example, the output device 114 may be a CPAP device worn by the user. In response to identifying sleep apnea as the abnormal sleep condition, the wearable device 110 may send to the output device 114 a signal that causes a controller of the output device 114 to increase the air pressure applied to the user's airway.

In yet another example, the wearable device 110 may determine from the plurality of physiological parameter measurements that the user is asleep, and the wearable device 110 may determine that a movement of the wearable device 110 is threshold high. When the wearable device 110 determines that the movement is threshold high, the wearable device 110 may identify sleepwalking as the abnormal sleep condition. The wearable device 110 may responsively apply a medium- or intensity vibration, or perhaps a high-intensity vibration, to the user. Additionally or alternatively, if the wearable device 110 and/or one or more output devices 114 includes a speaker, the wearable device 110 may provide and/or cause the output device(s) to provide audible alarms, which may be sufficiently loud enough to wake the user and/or individuals in the vicinity of the user. In this manner, the notification(s) may increase the likelihood of waking up the user before the user suffers an injury while sleepwalking.

Figure 3:
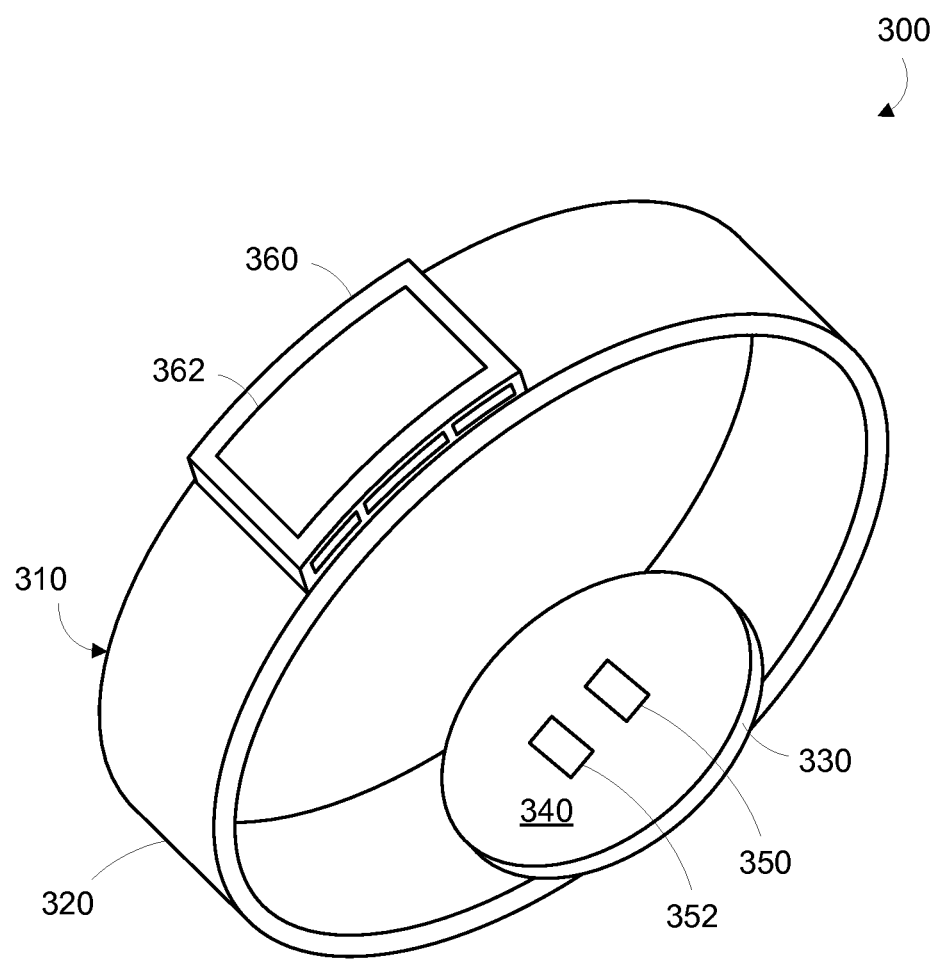
FIG. 3 is an example wearable electronic device.

As shown in FIG. 3, a wearable device 300 can automatically measure a plurality of physiological parameters of a person wearing the device. The term "wearable device," as used in this disclosure, refers to any device that is capable of being worn at, on or in proximity to a body surface, such as at a wrist, ankle, waist, chest, or other body part. In order to take in vivo measurements in a non-invasive manner from outside of the body, the wearable device 300 may be positioned on a portion of the body where subsurface vasculature is easily observable, the qualification of which will depend on the type of detection system used. A mount 310, such as a belt, wristband, ankle band, etc., can be provided to mount the wearable device 300 at, on, or in proximity to the body surface. The mount 310 may prevent the wearable device from moving relative to the body, thereby reducing measurement error and noise. The mount 310 could take the form of a strap or band 320 that the user wears around a body part. Further, the mount 310 may include an adhesive substrate for adhering the wearable device 300 to the user's body.

The measurement platform 330 may include one or more sensors configured to capture a measurement of at least one physiological parameter measurement. The at least one physiological parameter could be any parameter that may relate to the health of the person wearing the wearable device 300. For example, the wearable device 300 could be configured to measure blood pressure, pulse rate, respiration rate, skin temperature, Galvanic skin response, etc. The measurement platform 330 may thus be disposed on the mount 310 such that the measurement platform 330 is positioned on the body where subsurface vasculature is easily observable. When worn, an inner face 340 of the measurement platform 330 may face the body surface.

In one example, the sensor(s) may generate PPG signals from which the wearable device 300 may determine one or more physiological parameters. To this end, the measurement platform 330 may include on the inner face 340 a light emitter 350 and a light detector 352. Each PPG signal may include data indicative of detected light at one or more wavelengths, and the wearable device may be configured to determine values for one or more physiological parameters based on the intensity (or change in intensity) and wavelength of light received at the light detector 352. By way of example, the wearable device 300 may use the sensor to determine a heart rate, a heart rate variability, a respiration rate, a respiration rate variability, or the like.

In other examples, the measurement platform 330 may include one or more additional sensors, each of which may be configured to non-invasively measure one or more analytes in blood circulating in subsurface vasculature proximate to the wearable device. In a non-exhaustive list, the measurement platform 330 may include any one of an acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the measurement platform 330 may be miniaturized so that the wearable device may be worn on the body without significantly interfering with the wearer's usual activities.

In some examples, the measurement platform 330 may further include one or more additional signal sources, each of which may transmit an interrogating signal that can penetrate the wearer's skin into the portion of subsurface vasculature, for example, into a lumen of the subsurface vasculature. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the nanoparticle conjugates.

The wearable device 300 may also include a user interface 360 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 360 may include a display 362 where a visual indication of the alert or recommendation may be displayed. The display 362 may further be configured to provide an indication of the measured physiological parameters, for instance, the concentrations of certain blood analytes being measured.

Figure 4:
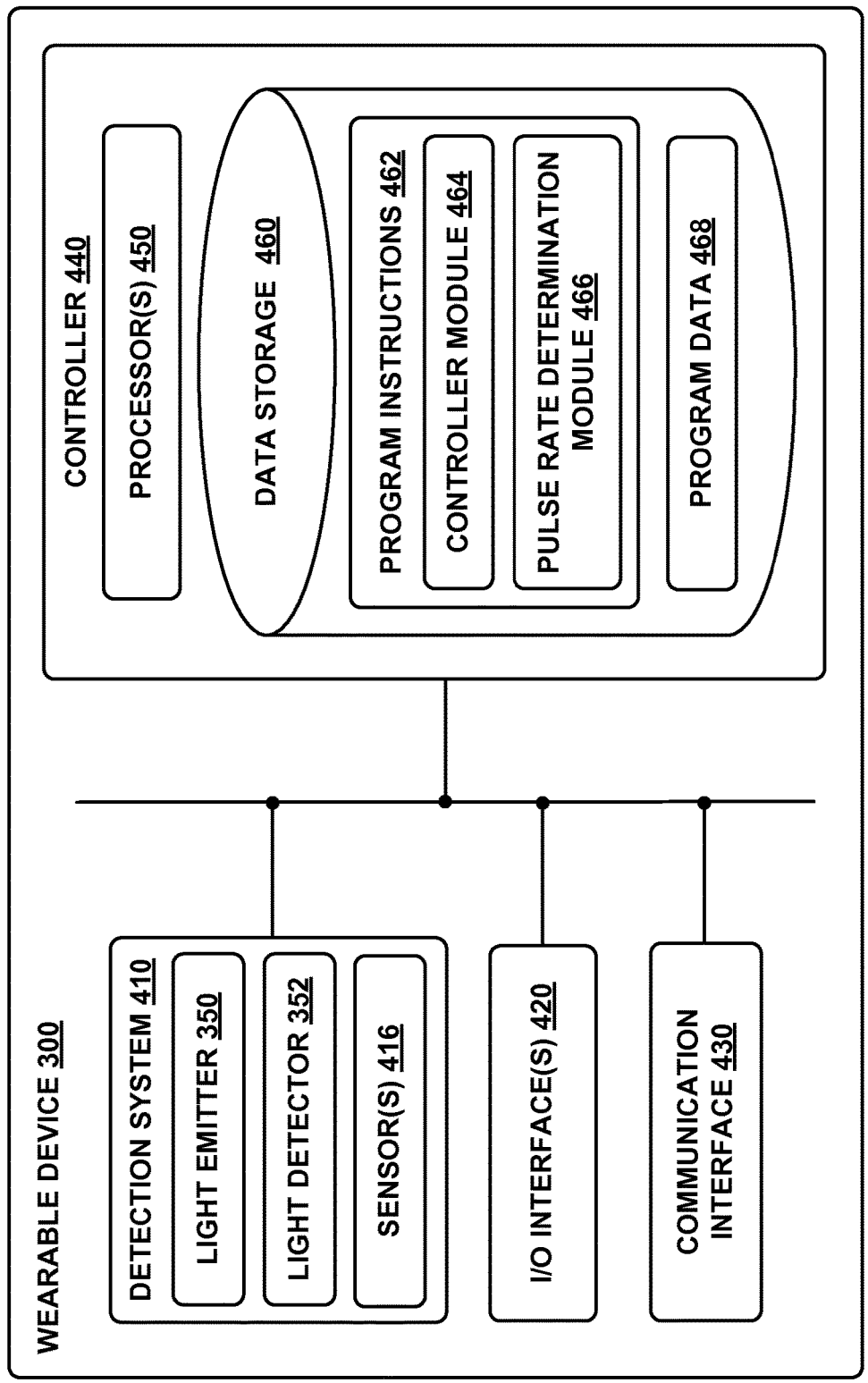
FIG. 4 is a functional block diagram of components disposed in an example wearable electronic device.

FIG. 4 is a simplified block diagram illustrating example components of the wearable device 300. In the illustrated example, the wearable device 300 includes a detection system 410, an input/output (I/O) interface 420, a communication interface 430 for transmitting data to a remote system, and a controller 440.

The controller 440 may be provided as a computing device that includes one or more processors 450. The one or more processors 450 can be configured to execute computer-readable program instructions 470 that are stored in the data storage 460 and that are executable to provide the functionality of a wearable device 300 described herein.

The data storage 460 may include or take the form of one or more non-transitory, computer-readable storage media that can be read or accessed by at least one processor 450. The one or more computer-readable storage media can include volatile and/or non-volatile storage components, such as optical, magnetic, organic or other memory or disc storage, which can be integrated in whole or in part with at least one of the one or more processors 450. In some embodiments, the computer readable data storage 460 can be implemented using a single physical device (e.g., one optical, magnetic, organic or other memory or disc storage unit), while in other embodiments, the computer readable data storage 460 can be implemented using two or more physical devices.

The detection system 410 includes the light emitter 350, the light detector 352, and one or more sensors 416. In line with the description above, the light emitter 350 is configured to emit illumination into an environment of interest (e.g., into a portion of subsurface vasculature), and light detector 352 is configured to detect one or more properties of light emitted from the portion of subsurface vasculature in response to illumination emitted from the light emitter 352. In a non-exhaustive list, the light detector 352 may include one or more of a photodiode, a phototransistor, a photoresistor, an active pixel sensor, a CCD, a camera, a spectrometer, an interferometer, or some other light sensitive element configured to detect one or more properties of the emitted light.

The detection system 410 could additionally include electronics configured to operate the light emitter 350 and the light detector 352. The electronics could include a high-speed analog-to-digital converter (ADC) configured to sample an output (e.g., a voltage, a current) of one or more light-sensitive elements of the light detector 352. Additionally or alternatively, the electronics could include analog frontend circuitry that includes analog circuitry configured to filter, decimate, quantize, or otherwise alter and/or perform other analog operations or computations on the output(s) of the light detector 352 to produce an output electronic signal that is related to physiological properties or other parameters in the environment. This output electronic signal(s) could then be used (e.g., sampled by an ADC of a microcontroller) to determine the cardiovascular pulse rate of a wearer.

The detection system 410 may additionally include one or more sensors 416 for detecting additional or alternative properties of the environment of interest (e.g., for detecting physiological parameters of a human whose body includes the environment of interest). Such additional detected properties could include any physiological parameters that may relate to the health of the person whose biological tissues are being measured by the wearable device 300. For example, the detection system 410 could include detectors configured to measure blood pressure, respiration rate, skin temperature, galvanic skin response, etc. In a non-exhaustive list, the one or more sensors 416 may include any one of an optical sensor, an acoustic sensor, an electrochemical sensor, a thermal sensor, a mechanical sensor, a magnetic sensor, and/or an electromagnetic sensor.

The one or more sensors 416 may include one or more devices for measuring one or more non-physiological parameters. By way of example, the one or more sensors 416 may include an IMU, which may itself include one or more accelerometers, gyrometers, and/or magnetometers. The IMU may measure a velocity and/or an acceleration of the wearable device in one or more dimensions, from which the IMU (or the one or more processors 450) may determine a movement of the wearable device. In As another example, the one or more sensors 416 may include a microphone. Note that the microphone could also be a component of the I/O interface 420.

The program instructions 462 stored on the data storage 460 may include instructions to perform any of the methods described herein. For instance, in the illustrated embodiment, program instructions 462 include a controller module 464 and a pulse rate determination module 466.

The controller module 464 can include instructions for operating the detection system 410, for example, the light emitter 350 and the light detector 352. For example, the controller module 464 may operate the light emitter 350 and the light detector 414 at a plurality of points in time to obtain a respective plurality of samples of a PPG signal. In particular, the controller module 464 can include instructions for operating the light emitter 350 to emit illumination into a target environment (e.g., tissue of a person) and for controlling the light detector 352 to detect an intensity, a wavelength, and/or other properties of light emitted from the environment responsive to the illumination.

The controller module 464 can also include instructions for operating the I/O interface 420. For example, the controller module 464 may include instructions for displaying data collected by the detection system 410 and analyzed by the pulse rate determination module 466. Further, the controller module 464 may include instructions to execute certain functions based on inputs accepted by the I/O interface 420, such as inputs accepted by one or more buttons or touchscreen displays disposed on the user interface.

The pulse rate determination module 466 may include instructions for receiving data from and/or operating the detection system 410, analyzing the data to determine pulse and/or respiratory rates, determining from such pulse/respiratory rates a sleep stage, identifying an abnormal sleep condition, or other analytical processes relating to the environment proximate to the wearable device 300.

Some of the program instructions of the controller module 464 and the pulse rate determination module 466 may, in some examples, be stored in a computer-readable medium and executed by a processor located external to the wearable device 300. For example, the wearable device 300 could be configured to illuminate and to receive light from portion of biological tissue (or to otherwise generate or obtain a plurality of samples of a signal of interest) and then transmit related data to a remote server, which may include a mobile device, a personal computer, the cloud, or any other remote system, for further processing (e.g., for the determination of pulse rates and/or frequencies of oscillating patterns in the received light using methods described herein).

I/O interface 420 could include indicators, displays, buttons, touchscreens, head-mounted displays, microphones, and/or other elements configured to present information about the wearable device 300 to a user and/or to allow the user to operate the wearable device 300. Additionally or alternatively, the wearable device 300 could be configured to communicate with another system (e.g., a cellphone, a tablet, a computer, a remote server) and to present elements of a user interface using the remote system. The I/O interface 420 could be configured to allow a user to specify some operation, function, or property of operation of the wearable device 300. The I/O interface 420 could be configured to present a determined pulse rate of blood in a portion of subsurface vasculature or some other health state of a wearer of the wearable device 300, or to present some other information to a user. Other configurations and methods of operation of the I/O interface 420 are anticipated.

Communication interface 430 may also be operated by instructions within the program instructions 462, such as instructions for sending and/or receiving information via a wireless antenna, which may be disposed on or in the wearable device 300. The communication interface 430 can optionally include one or more oscillators, mixers, frequency injectors, etc. to modulate and/or demodulate information on a carrier frequency to be transmitted and/or received by the antenna. In some examples, the wearable device 300 is configured to indicate an output from the controller 440 by transmitting an electromagnetic or other wireless signal according to one or more wireless communications standards (e.g., Bluetooth®, WiFi®, IRdA®, ZigBee®, WiMAX®, LTE®). In some examples, the communication interface 430 could include one or more wired communications interfaces and the wearable device 300 could be configured to indicate an output from the controller 440 by operating the one or more wired communications interfaces according to one or more wired communications standards (e.g., USB, FireWire, Ethernet, RS-232).

The data storage 460 may further contain other data or information, such as scattering, absorption, or other optical properties of tissues of a user of the wearable device 300, that may be useful in determining pulse rates or other physiological parameters. Further, the data storage 460 may contain data corresponding to pulse rate transition probabilities or other property baselines that describe expected changes in cardiovascular pulse rate or other properties of biological tissues and/or of a body. The baselines may be pre-stored on the data storage 460, may be transmitted from a remote source, such as a remote server, or may be generated by the pulse rate determination module 466 itself.

The pulse rate determination module 466 may include instructions for generating individual baselines for the user of the wearable device 300 based on data collected over a certain period of time. For example, the pulse rate determination module 466 may generate a baseline set of transition probabilities or other statistics describing expected changes in pulse rate over time based on cardiovascular pulse determined based on PPG signals detected from portions of subsurface vasculature. The pulse rate determination module 466 could store those baselines in the data storage 460 for later use (e.g., to apply a forward-backward filter to a set of determined pulse rates or to perform some other filtering or determination related to a cardiovascular pulse). Baselines may also be generated by a remote server and transmitted to the wearable device 300 via the communication interface 430.

In some examples, obtained samples of a PPG signal or other physiological property or parameter of interest, determined pulse rates, or other information generated by the wearable device 300 may additionally be input to a cloud network and be made available for download by a user's physician. Analyses may also be performed on the collected data, such as estimates of pulse rate variability, arrhythmia, determinations of post-surgical treatment or rehabilitation regimens, and/or efficacy of drug treatment regimens, in the cloud computing network and be made available for download by physicians or clinicians. Further, collected information from individuals or populations of device users may be used by physicians or clinicians in monitoring efficacy of a surgical intervention or other treatment.

Figure 5A:
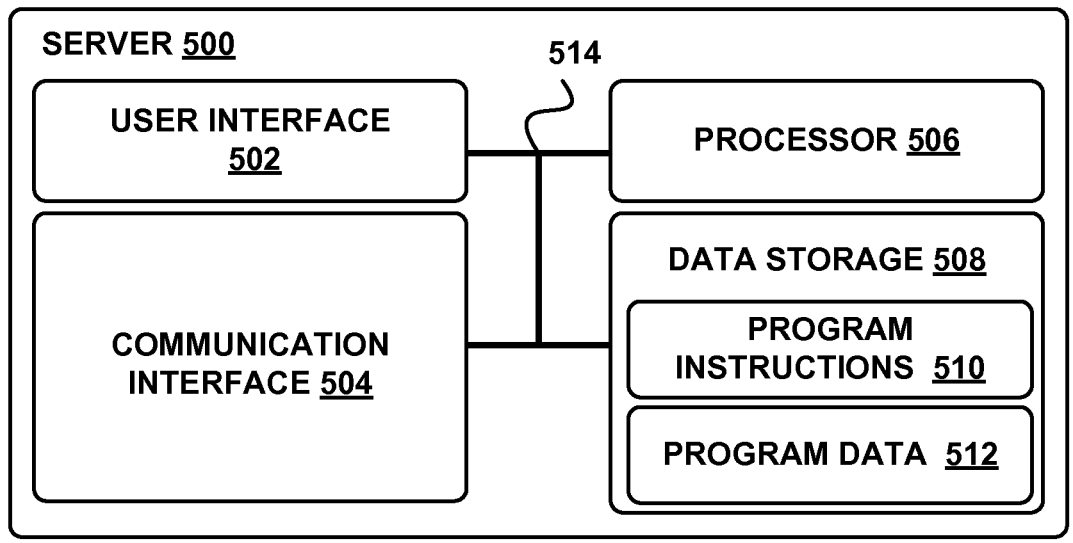
FIG. 5A is a block diagram of an example server.

Turning now to FIG. 5A, a block diagram of a server in accordance with an example embodiment is shown. In particular, server 500 shown in FIG. 5A can be configured to perform one or more functions of server 130 and/or server data storage 132. Server 500 may include a user interface 502, a communication interface 504, a processor 506, and/or data storage 508, all of which may be linked together via a system bus, network, or other connection mechanism 514.

The user interface 502 may include user input devices such as a keyboard, a keypad, a touch screen, a computer mouse, a track ball, a joystick, and/or other similar devices, now known or later developed. The user interface 502 may also include user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. Additionally, the user interface 502 may be configured to generate audible output(s), via a speaker, speaker jack, audio output port, audio output device, earphones, and/or other similar devices, now known or later developed. In some embodiments, the user interface 502 may include software, circuitry, or another form of logic that can transmit data to and/or receive data from external user input/output devices.

The communication interface 504 may include one or more wireless interfaces and/or wireline interfaces that are configurable to communicate via a network, such as network 108 shown in FIG. 1. The wireless interfaces, if present, may include one or more wireless transceivers, such as a BLUETOOTH® transceiver, a WiFi® transceiver perhaps operating in accordance with an IEEE 802.11 standard (e.g., 802.11b, 802.11g, 802.11n), a WiMAX transceiver perhaps operating in accordance with an IEEE 802.16 standard, a Long-Term Evolution (LTE) transceiver perhaps operating in accordance with a 3rd Generation Partnership Project (3GPP) standard, and/or other types of wireless transceivers configurable to communicate via local-area or wide-area wireless networks. The wireline interfaces, if present, may include one or more wireline transceivers, such as an Ethernet transceiver, a Universal Serial Bus (USB) transceiver, or similar transceiver configurable to communicate via a twisted pair wire, a coaxial cable, a fiber-optic link or other physical connection to a wireline device or network. Other examples of wireless and wireline interfaces may exist as well.

The processor 506 may include one or more general purpose processors (e.g., microprocessors) and/or one or more special purpose processors (e.g., digital signal processors (DSPs), graphical processing units (GPUs), floating point processing units (FPUs), network processors, or application specific integrated circuits (ASICs)). The processor 506 may be configured to execute computer-readable program instructions 510 that are contained in data storage 408, and/or other instructions, to carry out various functions described herein.

Thus, the data storage 508 may include one or more non-transitory computer-readable storage media that can be read or accessed by the processor 506. The one or more computer-readable storage media may include volatile and/or non-volatile storage components, such as optical, magnetic, organic or other memory or disc storage, which can be integrated in whole or in part with the processor 506. In some embodiments, the data storage 508 may be implemented using a single physical device (e.g., one optical, magnetic, organic or other memory or disc storage unit), while in other embodiments, the data storage 508 may be implemented using two or more physical devices.

Data storage 508 may also include the program data 512 that can be used by processor 506 to carry out functions described herein. In some embodiments, the data storage 508 may include, or have access to, additional data storage components or devices (e.g., cluster data storages described below).

Figure 5B:
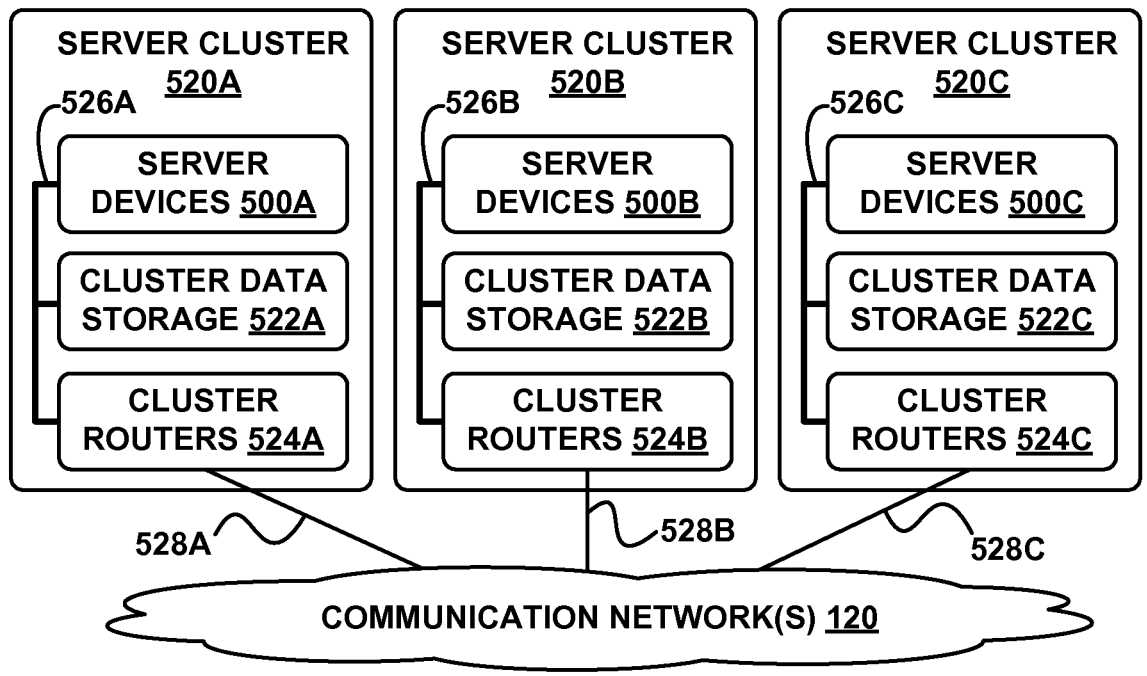
FIG. 5B is a block diagram of an example cloud-based server system.

FIG. 5B depicts a cloud-based server in accordance with an example embodiment. In FIG. 5B, functions of server 130 and server data storage device 132 may be distributed among three server clusters 520A, 520B, and 520C. Server cluster 520A may include one or more server devices 500A, cluster data storage 522A, and cluster routers 524A connected by a local cluster network 526A. Similarly, server cluster 520B may include one or more server devices 500B, cluster data storage 522B, and cluster routers 524B connected by a local cluster network 526B. Likewise, server cluster 520C may include one or more server devices 500C, cluster data storage 522C, and cluster routers 524C connected by a local cluster network 526C. Server clusters 520A, 520B, and 520C may communicate with network 108 via communication links 528A, 528B, and 528C, respectively.

In some embodiments, each of the server clusters 520A, 520B, and 520C may have an equal number of servers, an equal number of cluster data storages, and an equal number of cluster routers. In other embodiments, however, some or all of the server clusters 520A, 520B, and 520C may have different numbers of servers, different numbers of cluster data storages, and/or different numbers of cluster routers. The number of servers, cluster data storages, and cluster routers in each server may depend on the computing task(s) and/or applications assigned to each server.

In the server cluster 520A, for example, server devices 500A can be configured to perform various computing tasks of server 130. In one embodiment, these computing tasks can be distributed among one or more of server devices 500A. Server devices 500B and 400C in server clusters 520B and 520C may be configured the same or similarly to server devices 500A in server clusters 520A. On the other hand, in some embodiments, server devices 500A, 500B, and 500C each may be configured to perform different functions. For example, server devices 500A may be configured to perform one or more functions of server 130, and server devices 500B and server devices 500C may be configured to perform functions of one or more other servers. Similarly, the functions of server data storage device 132 can be dedicated to a single server, or spread across multiple servers.

Cluster data storages 522A, 522B, and 522C of the server clusters 520A, 520B, and 520C, respectively, may be data storage arrays that include disk array controllers configured to manage read and write access to groups of hard disk drives. The disk array controllers, alone or in conjunction with their respective servers, may also be configured to manage backup or redundant copies of the data stored in cluster data storages to protect against disk drive failures or other types of failures that prevent one or more servers from accessing one or more cluster data storages.

Similar to the manner in which the functions of server 130 and server data storage device 132 can be distributed across server clusters 520A, 520B, and 520C, various active portions and/or backup/redundant portions of these components can be distributed across cluster data storages 522A, 522B, and 522C. For example, some cluster data storages 522A, 522B, and 522C may be configured to store backup versions of data stored in other cluster data storages 522A, 522B, and 522C.

Cluster routers 524A, 524B, and 524C in server clusters 520A, 520B, and 520C, respectively, may include networking equipment configured to provide internal and external communications for the servers. For example, cluster routers 524A in server cluster 520A may include one or more packet-switching and/or routing devices configured to provide (i) network communications between servers 500A and cluster data storage 522A via cluster network 526A, and/or (ii) network communications between the server cluster 520A and other devices via communication link 528A to communication network 120. Cluster routers 524B and 524C may include network equipment similar to cluster routers 524A, and cluster routers 524B and 524C may perform networking functions for server clusters 520B and 520C that cluster routers 524A perform for server 520A.

Additionally, the configuration of cluster routers 524A, 524B, and 524C can be based at least in part on the data communication requirements of the servers and cluster storage arrays, the data communications capabilities of the network equipment in the cluster routers 524A, 524B, and 524C, the latency and throughput of the local cluster networks 526A, 526B, 526C, the latency, throughput, and cost of the wide area network connections 528A, 528B, and 528C, and/or other factors that may contribute to the cost, speed, fault-tolerance, resiliency, efficiency and/or other design goals of the system architecture.

III. EXAMPLE METHODS

Figure 6:
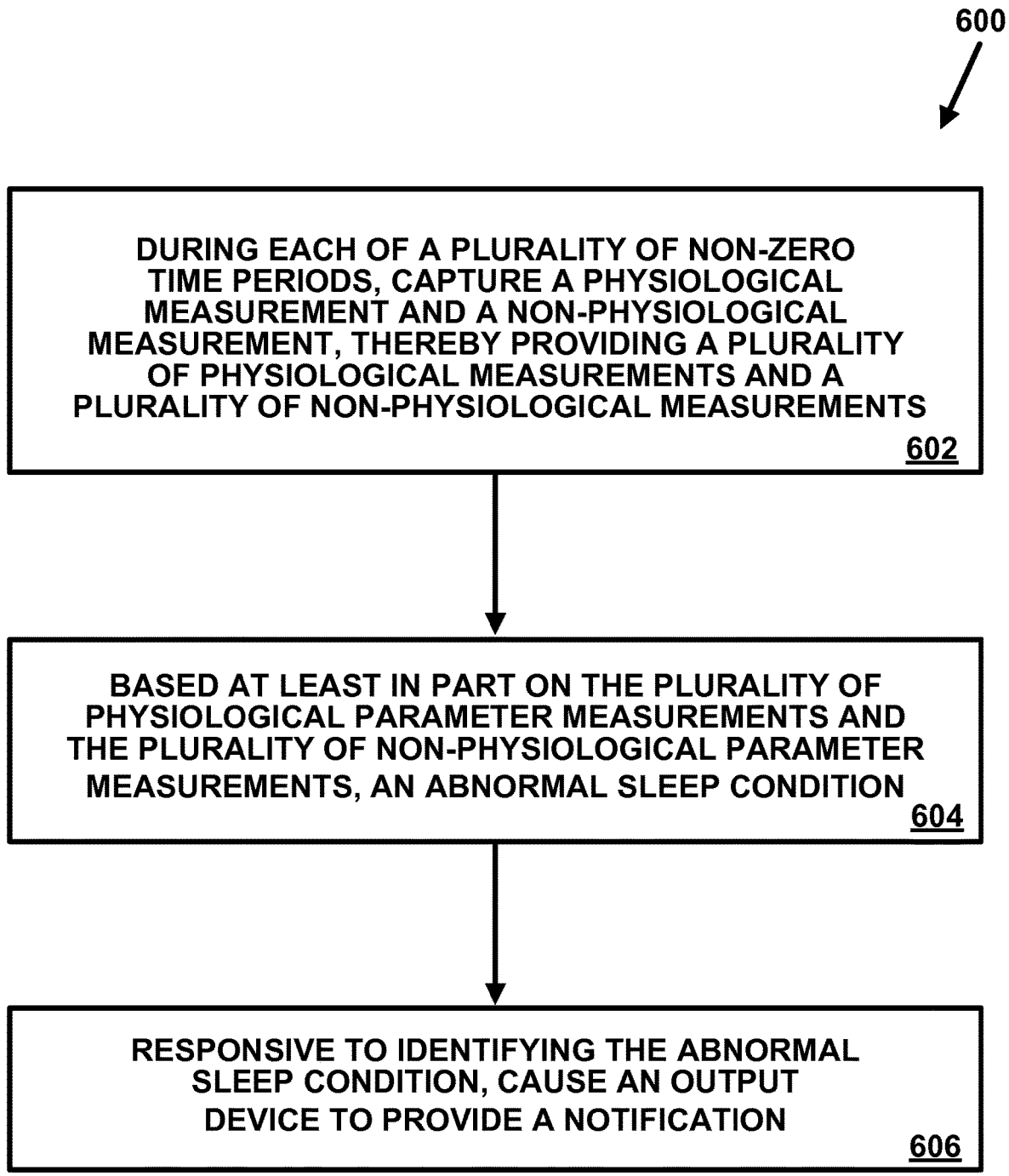
FIG. 6 is a flowchart of an example method.

Turning now to FIG. 6, a flow diagram of an example method 600 is shown. A component of a health monitoring system, such as anyone of the wearable devices 110, 200, or 300, servers 130, 500, or servers 500A-500C, may implement the functions of the method 600 to identify an abnormal sleep condition and, responsive to identifying the abnormal sleep condition, to cause a device to provide a notification. Alternatively, multiple components of the health monitoring system may implement the functions of the method 600. Functions described in blocks of the flowchart may be provided as instructions stored on a non-transitory computer readable medium that can be executed by a computing system to perform the functions.

Beginning at block 602, the method 600 includes a wearable device capturing, during each of plurality of non-zero time periods, a physiological parameter measurement and a non-physiological parameter measurement, thereby providing a plurality of physiological parameter measurements and a plurality of non-physiological parameter measurements. By way of example, each physiological parameter measurement may be a PPG signal. In this example, the non-zero time period may be sufficiently long enough to generate a PPG signal, such as about thirty seconds. In other examples, the non-zero time period may be longer or shorter than thirty seconds. Moreover, the physiological parameter measurement could be a different measurement, such as an electrocardiogram, a nuclear magnetic resonance signal, a galvanic skin response, a skin temperature, or another physiological parameter.

The non-physiological parameter may be a movement of the wearable device during the non-zero time period. As one example, a wearable device may include a sensor such as an IMU that measures the movement of the wearable device in one or more dimensions. As another example, the wearable device may include a microphone, in which case the non-physiological parameter may be a recorded audio signal. Other examples of non-physiological parameters may also be possible.

Based at least in part on the plurality of physiological parameter measurements and the plurality of non-physiological parameter measurements, the method 600 includes the wearable device identifying, an abnormal sleep condition, at block 604. When performing the functions of block 604, the wearable device may extract one or more of physiological parameters from each physiological parameter measurement. In an example in which the plurality of physiological parameter measurements includes PPG signals, the wearable device may perform a transform on each PPG signal, perhaps by performing a fast Fourier transform on the PPG signal. The wearable device may then extract from each transformed PPG signal one or more physiological parameters. By way of example, the extracted physiological parameters may include a pulse rate and/or a respiration rate. The wearable device may then determine a plurality of pulse/respiration rate means and a plurality of pulse/respiration variances, with each pulse/respiration rate mean and each pulse/respiration rate variance being determined from a set of pulse/respiration rates extracted from consecutively measured PPG signals (e.g., the PPG signal at time t, the PPG signal at time t+1, the PPG signal at time t+2, etc.) As one non-limiting example, the wearable device may determine each mean and variance from fifteen consecutively measured PPG signals.

The wearable device may also determine whether a non-physiological parameter measurement is threshold high when performing the functions of block 604. As one example, the non-physiological parameter may be a measured movement of the wearable device, and the threshold may correspond to a movement (e.g., a change in the position, velocity, and/or acceleration from the time at which the user began sleeping) indicative of the user walking. Determining whether or not the measured movement is threshold high may thus provide an indication of whether the user is walking or otherwise changing position. As another example, the non-physiological measurement may be audio recorded by the wearable device. Comparing the non-physiological measurement to the threshold may include determining that an amplitude of the sound recorded over the period of time is threshold high. In this case, the threshold may be sufficiently high amplitude to be indicative of the user snoring. Further, the wearable device may determine that the sound includes a frequency spectrum profile that corresponds to the user snoring.

To identify an abnormal sleeping condition, the wearable device may determine a sleep stage by comparing one or more vectors (each of which may include multiple extracted physiological parameters and non-physiological measurements) to a range of vectors that correlates to a particular sleep stage. As one example, the wearable device may determine from the plurality of non-physiological parameter measurements that the user is lying on the user's back and/or snoring, and the wearable device may determine from each of the physiological parameter measurements that the user is in stage 3 NREM sleep or REM sleep. From these determinations, the wearable device may identify sleep apnea as the abnormal sleeping condition. As another example, the wearable device may determine from one or more vectors that the user is asleep (e.g., in one of the four NREM sleep stages or in REM sleep). The wearable device may also determine from the plurality of non-physiological the user is walking. The wearable device may thus identify sleepwalking as the abnormal sleep condition. These are but two, non-limiting examples of abnormal sleep conditions. A server implementing a machine-learning algorithm may determine, for each of a plurality of abnormal sleep conditions, corresponding sets of vectors and non-physiological parameter measurements that are indicative of a particular abnormal sleep condition.

While the wearable device performs the functions the block 604 in the preceding examples, a server could also perform the functions of block 604. By way of example, the wearable device may send to the server the plurality of physiological parameter measurements and the plurality of non-physiological parameter measurements. The server may then identify the abnormal sleeping condition and send to the wearable device a signal that includes data indicative of the identity of the abnormal sleeping condition.

Responsive to identifying the abnormal sleep condition, the method 600 includes causing a component connected to the wearable device to provide a notification. The notification may depend on the identified abnormal sleep condition. For example, if sleep apnea is the abnormal sleep condition, the notification may be a vibration applied to the user's skin at an intensity level sufficient to cause the user to roll on to the user's side without waking the user. The wearable device may include an output device configured to provide the notification, or the wearable device may be connected to an external device configured to provide a vibration to the user. As another example, the wearable device may be connected to a CPAP device. In this case, the wearable device may send a signal to the CPAP device. Responsive to receiving the signal, the CPAP may increase an air pressure applied to the user's airway, thereby allowing the user to sleep without waking.

In an example in which the sleepwalking is the abnormal sleeping condition, the wearable device may cause the component to provide the notification as a vibration of sufficient intensity to wake the user. Additionally, the wearable device may provide the notification as an audio output. In this case, the wearable device may output an audio output from an integrated speaker and/or a speaker of one or more devices connected to the wearable device. In this manner, the notification(s) may also wake individuals near the user.

In addition to providing a notification, the wearable device may send one or more additional signals to devices connected to the wearable device. For instance, the wearable device may send messages to one or more other devices, such as the user's smartphone (or similar computing device) and/or a physician's smartphone (or similar computing device). The message may include data indicative of the plurality of physiological parameter measurements and/or the plurality of non-physiological parameter measurements.

IV. CONCLUSION

Where example embodiments involve information related to a person or a device of a person, the embodiments should be understood to include privacy controls. Such privacy controls include, at least, anonymization of device identifiers, transparency, and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the figures should not be viewed as limiting. It should be understood that other embodiments may include more or less of each element shown in a given figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:
1. A method comprising:
during each of a plurality of non-zero time periods, measuring by a wearable device at least one physiological parameter and at least one non-physiological parameter, thereby providing a plurality of measurements of the at least one physiological parameter and a plurality of measurements of the at least one non- physiological parameter, wherein the wearable device is configured to be worn on a body of a user;

receiving from a server, by the wearable device, a vector that correlates ranges and/or thresholds for the at least one physiological parameter and for the at least one non-physiological parameter to an abnormal sleep condition;

based at least in part on the plurality of measurements of the at least one physiological parameter, the plurality of measurements of the at least one non-physiological parameter, and the vector, identifying by the wearable device the abnormal sleep condition; and responsive to identifying the abnormal sleep condition, causing by the wearable device an output device to provide a notification.

2. The method of claim 1, wherein the plurality of measurements of the at least one physiological parameter includes a plurality of photoplethysmographic signals.

3. The method of claim 1, wherein the at least one physiological parameter includes a heart rate or a respiration rate.

4. The method of claim 1, wherein the output device comprises a control unit for an apparatus configured to provide a positive air pressure to the user's airway, and wherein the notification is an increase in the positive air pressure applied by the apparatus.

5. The method of claim 1, wherein the plurality of measurements of the at least one non-physiological parameter includes a plurality of audio signals, and wherein identifying the abnormal sleep condition comprises determining that at least one of the plurality of audio signals includes a sound indicative of snoring.

6. The method of claim 1, wherein the output device comprises an electro-mechanical transducer, and wherein the notification is a vibration applied to the user by the electro-mechanical transducer.

7. The method of claim 1, wherein measurements of the at least one non-physiological parameter includes data indicative of a movement of the wearable device, and wherein identifying the abnormal sleep condition comprises determining, from the data indicative of the movement of the wearable device, that the user is supine.

8. The method of claim 1, wherein the plurality of measurements of the at least one non-physiological parameter includes data indicative of movement of the wearable device, and wherein identifying the abnormal sleep condition comprises (i) determining from the data indicative of movement of the wearable device that the user is walking, and (ii) determining from the plurality of measurements of the at least one physiological parameter that the user is asleep.

9. A wearable device comprising:
a communication interface;
a first sensor configured to measure a physiological parameter;
a second sensor configured to measure a non-physiological parameter; and
a processor configured to:
during each of a plurality of non-zero time periods, (a) receive from the first sensor a measurement of the physiological parameter, thereby receiving a plurality of measurements of the physiological parameter, and (b) receive from the second sensor a measurement of the non-physiological parameter, thereby receiving a plurality of measurements of the non-physiological parameter;

receive from a server, via the communication interface, a vector that correlates ranges and/or thresholds for the physiological parameter and for the non-physiological parameter to an abnormal sleep condition; and based at least in part on the plurality of measurements of the physiological parameter, the plurality of measurements of the non-physiological parameter, and the vector, identify the abnormal sleep condition.

10. The wearable device of claim 9, wherein the first sensor measures the physiological parameter as a photoplethysmographic signal.

11. The wearable device of claim 9, wherein the physiological parameter is a heart rate or a respiration rate.

12. The wearable device of claim 9, wherein the processor is further configured to send a signal to a remote output device via the communication interface in response to identifying the abnormal sleep condition, wherein the signal causes the remote output device to provide a notification.

13. The wearable device of claim 9, wherein the plurality of measurements of the non-physiological parameter includes a plurality of audio signals, and wherein identifying the abnormal sleep condition comprises determining that at least one audio signal includes a sound indicative of snoring.

14. The wearable device of claim 9, further comprising an output device configured to provide a notification, and wherein the processor is further configured to cause, in response to identifying the abnormal sleep condition, the output device to provide the notification.

15. The wearable device of claim 9, wherein the plurality of measurements of the non-physiological parameter includes data indicative of a movement of the wearable device, and wherein identifying the abnormal sleep condition comprises determining, from the data indicative of the movement of the wearable device, that the user is supine.

16. The wearable device of claim 9, wherein the second sensor is configured to measure a movement of the wearable device, wherein the plurality of measurements of the non-physiological parameter includes data indicative of movement of the wearable device, and wherein, to identify the abnormal sleep condition, the processor is configure to (i) determine from the data indicative of movement of the wearable device that the user is walking, and (ii) determine from the plurality of physiological measurements that the user is asleep.

17. The method of claim 1, further comprising:
receiving from the server, by the wearable device, a plurality of vectors for a plurality of abnormal sleep conditions, wherein each vector of the plurality of vectors correlates respective ranges and/or thresholds for the at least one physiological parameter and for the at least one non-physiological parameter to a respective abnormal sleep condition of the plurality of abnormal sleep conditions.

18. The method of claim 1, wherein the plurality of abnormal sleep conditions includes sleep apnea and sleepwalking.

19. The wearable device of claim 9, wherein the processor is further configured to:
receive from the server, via the communication interface, a plurality of vectors for a plurality of abnormal sleep conditions, wherein each vector of the plurality of vectors correlates respective ranges and/or thresholds for the physiological parameter and for the non-physiological parameter to a respective abnormal sleep condition of the plurality of abnormal sleep conditions.

20. The wearable device of claim 19, wherein the plurality of abnormal sleep conditions includes sleep apnea and sleepwalking.

\* \* \* \* \*